United States Patent
Birke et al.

(10) Patent No.: US 9,573,863 B2
(45) Date of Patent: Feb. 21, 2017

(54) PROCESS AND PLANT FOR THE PRODUCTION OF LOWER-MOLECULAR OLEFINS

(75) Inventors: Gerhard Birke, Frankfurt (DE); Hermann Bach, Heiligenroth (DE)

(73) Assignee: Lurgi GmbH, Frankfurt am Main (DE)

( * ) Notice: Subject to any disclaimer, the term of this patent is extended or adjusted under 35 U.S.C. 154(b) by 470 days.

(21) Appl. No.: 14/006,908

(22) PCT Filed: Feb. 7, 2012

(86) PCT No.: PCT/EP2012/052040
§ 371 (c)(1),
(2), (4) Date: Sep. 23, 2013

(87) PCT Pub. No.: WO2012/126670
PCT Pub. Date: Sep. 27, 2012

(65) Prior Publication Data
US 2014/0018593 A1   Jan. 16, 2014

(30) Foreign Application Priority Data
Mar. 23, 2011 (DE) .................. 10 2011 014 892

(51) Int. Cl.
C07C 1/20 (2006.01)
C07C 2/86 (2006.01)
C07C 4/06 (2006.01)

(52) U.S. Cl.
CPC .............. C07C 2/864 (2013.01); C07C 1/20 (2013.01); C07C 4/06 (2013.01); C07C 2529/40 (2013.01); Y02P 20/582 (2015.11); Y02P 30/42 (2015.11)

(58) Field of Classification Search
CPC .............. C07C 1/00; C07C 1/20; C07C 4/06; C07C 11/04; C07C 11/06; C07C 2529/40; C07C 2/864
USPC ................... 585/638, 639, 640, 641
See application file for complete search history.

(56) References Cited

U.S. PATENT DOCUMENTS

| 8,444,940 | B2 * | 5/2013 | Bach .................. B01J 4/002 422/618 |
| 2003/0181777 | A1 | 9/2003 | Powers et al. |
| 2004/0019246 | A1 * | 1/2004 | Van Egmond ............ C07C 1/20 585/639 |
| 2004/0087824 | A1 | 5/2004 | O'Rear et al. |
| 2009/0124841 | A1 | 5/2009 | Rothaemel et al. |
| 2009/0137856 | A1 | 5/2009 | Birke et al. |
| 2010/0063337 | A1 | 3/2010 | Bach et al. |
| 2010/0179365 | A1 * | 7/2010 | Ito ........................ B01J 29/40 585/639 |
| 2010/0206771 | A1 | 8/2010 | Rothaemel et al. |

FOREIGN PATENT DOCUMENTS

| DE | 3524890 | 1/1986 |
| EP | 2058290 | 5/2009 |
| WO | 2008039552 | 4/2008 |

OTHER PUBLICATIONS

International Search Report from European Patent Office, from International Application PCT/EP2012/05204-, corresponding to this new filing, mailed Apr. 4, 2012, pp. 1-4.
International Preliminary Report on Patentability, for PCT/EP2012/052040 corresponding to U.S. Appl. No. 14/006,908, mailed Oct. 3, 2013 (14 pages).

* cited by examiner

Primary Examiner — Sharon Pregler
(74) Attorney, Agent, or Firm — Pauly, Devries Smith & Deffner, LLC

(57) ABSTRACT

In the production of low-molecular olefins, in particular of ethylene and propylene, an educt stream (O) containing at least one oxygenate and an educt stream (C) containing at least one $C_{4+}$ olefin are simultaneously converted in at least one identical reactor on an identical catalyst to obtain a product mixture (P) comprising low-molecular olefins and gasoline hydrocarbons. The ratio (V) of oxygenates in the educt stream (O) to $C_{4+}$ olefins in the educt stream (C) here is 0.05 to 0.5 and is calculated according to the following formula:

$$V = \frac{\sum_j k_{oxygenate-j} * n_{oxygenate-j}}{\sum_i k_{olefin-i} * n_{olefin-i} + \sum_j k_{oxygenate-j} * n_{oxygenate-j}}$$

with:
$k_{oxygenate-j}$: carbon number of the oxygenate j
$n_{oxygenate-j}$: molar flow rate of the oxygenate j
$k_{olefin-i}$: carbon number of the olefin i
$n_{olefin-i}$: molar flow rate of the olefin i.

14 Claims, 5 Drawing Sheets

US 9,573,863 B2

PROCESS AND PLANT FOR THE PRODUCTION OF LOWER-MOLECULAR OLEFINS

CROSS-REFERENCE TO RELATED APPLICATIONS

This application is a national stage application under 35 U.S.C. 317 of Inter-national Patent Application Serial No. PCT/EP2012/052040, entitled "VERFAHREN UND ANLAGE ZUR HERSTELLUNG VON NIEDERMOLE-KULAREN OLEFINEN," filed Feb. 15, 2012, the disclosure of which is incorporated herein by reference.

FIELD OF THE INVENTION

The present invention relates to a process for the production of short-chain or low-molecular olefins, in particular of ethylene and propylene, wherein an educt stream containing at least one oxygenate and an educt stream containing at least one $C_{4+}$ olefin are simultaneously converted in at least one identical reactor on an identical catalyst to obtain a product mixture containing low-molecular olefins and gasoline hydrocarbons. Furthermore, the present invention also relates to a plant suitable for carrying out the process.

BACKGROUND

Propene ($C_3H_6$), often also referred to as propylene, is one of the most important starting substances of the chemical industry. The demand for the base material propylene is increasing worldwide, wherein propylene just like ethylene mostly is produced from petroleum in a steam cracker in a ratio dependent on the process and the raw materials.

To obtain additional propylene, a number of processes exist, such as the PDH process which proceeds from propane as educt. However, since the largest part of propylene still is produced by steam cracking (about 70%), there is a tendency to convert the $C_4$ to $C_8$ olefins obtained in crackers or other petrochemical plants to additional propylene, in part also to ethylene.

On the one hand, this can be effected via the metathesis process, which is based on a synproportionation of ethylene and butylene. It is disadvantageous here that for this purpose the ethylene production must be increased and only $C_4$ olefins can be converted.

Furthermore, an olefin conversion is possible, in which $C_{4+}$ olefins are converted to propylene. Such cracking is effected by means of the Propylur or OCP process and above all is employed to utilize the $C_{4+}$ olefins produced in a cracker plant—which are to be valued comparatively low—for the production of propylene. Due to the endothermicity of the reaction, the temperature in the reactor however decreases with increasing conversion and thus limits the achievable propylene yield.

Finally, the methanol-to-propylene process (also MTP® process) is recommendable, in which methanol/dimethyl ether or also other oxygenates are converted to propylene on a mostly zeolitic catalyst.

DE 10 2005 048 931 describes such MTP® process for the production of $C_2$ to $C_4$ olefins from an educt mixture containing steam and oxygenates, such as methanol and/or dimethyl ether, in which the educt mixture is converted in at least one reactor by a heterogeneously catalyzed reaction to obtain a reaction mixture comprising low-molecular olefins and gasoline hydrocarbons. In a first separating means, this reaction mixture then is separated into a mixture rich in $C_{5-}$ olefins, a fraction rich in $C_{5+}$ gasoline hydrocarbons, and an aqueous phase. The fraction rich in $C_{5+}$ gasoline hydrocarbon afterwards is supplied to a second separating means in which the aromatics are removed from the mixture. The remaining residual stream largely free of aromatics is at least partly recirculated into the reactor as recycling stream. This has the advantage that the olefin fraction for the most part can be converted to propylene, whereby the yield of propylene as a whole is increased.

WO 2008/039552 A1 teaches a process in which MTP® and cracking processes are connected in series. For this purpose, the oxygenates are converted into olefins in a reactor according to the MTP® process. From the product stream thus obtained, ethylene and propylene are separated. In this separation, remaining oxygenates and water also are removed from the stream, whereby a pure $C_{4+}$ fraction is obtained, which is transferred into an olefin cracking reactor. By cracking the olefins, further ethylene and propylene can then be obtained.

US 2004/008 7824 A1 describes a combination of the two processes for converting oxygenates and for cracking olefins proceeding from the product mixture from a Fischer-Tropsch synthesis. For this purpose, the product stream which contains both oxygenates and $C_{6+}$ olefins is brought in contact with an acid, olefin-cracking catalyst. Both the oxygenates and the high-molecular olefins then are converted to light olefins such as propylene, butene and pentene. The conversion is effected at temperatures between 260 and 454° C. and a pressure below 69 bar. Due to these reaction conditions, however, there is still obtained a considerable $C_{4+}$ olefin fraction, whereas $C_4/C_5$ olefins are not significantly converted to lighter olefins and the valuable product ethylene can hardly be obtained.

The combination of an MTP® plant with a cracker plant is described in DE 10 2007 045 238 A1, wherein MTP® reactor and cracker are connected in parallel. The respective intermediate product streams of the steam cracker and the reactor are at least partly joined. This has the advantage that the succeeding separating means can be utilized jointly. Parts of these streams also are recirculated to the steam cracker and/or the MTP® reactor, whereby in particular in the MTP® reactor the longer-chain alkenes are cracked to lighter olefins, in particular ethylene and propylene.

With an interconnection according to DE 10 2007 045 238 A1, it is possible to produce 50,899 t.p.a. of ethylene and 440,331 t.p.a. of propylene more than in a pure cracker plant from 1,660,000 t.p.a of methanol in the combination of MTP® and cracker plants, and hence the ratio of $C_2$ to $C_3$ can effectively be shifted in favor of propylene from 43.06 to 1.86. However, the selectivity of the sum of the valuable products propylene and ethylene based on methanol only is about 0.68 and hence distinctly <1, from which it follows that the selectivity is only slightly larger than in a self-sufficient MTP® plant. This means that the increased yield of propylene chiefly is to be associated to the pure parallel connection of MTP® and cracker plant, and a substantial reduction of the olefins with higher C numbers present in the MTP®/cracker complex could not be effected.

From DE 10 2007 045 238 A1 it is also known that due to the presence of longer-chain olefins and as a result the occurrence of endothermal reactions, the temperature in the reactor can be lowered. However, it is not disclosed in the prior art in what ratio the streams of oxygenates and $C_{4+}$ olefins must be, in order to keep the temperature in the reactor at an almost constant level. A rather uniform temperature profile, however, is important because the cracking of olefins so far is limited by the fact that the endothermal reaction makes the temperature in the reactor decrease, so that finally there will not be sufficient energy to overcome the activation energy, and therefore the reaction does not proceed completely. At the same time, the classical MTP® process is highly exothermal, so that despite an expensive cooling construction the rising temperature in the reactor reduces the selectivity with regard to propylene.

Therefore, it is the object of the invention to provide a process in which a maximization of the yield of propylene and ethylene can be achieved by a rather homogeneous temperature profile.

SUMMARY

This object substantially is solved by the invention with the features of claim 1, in that an educt stream containing at least one oxygenate and an educt stream containing at least one $C_{4+}$ olefin are simultaneously converted in at least one identical reactor on an identical catalyst to obtain a product mixture containing low-molecular olefins and gasoline hydrocarbons. According to the invention, the ratio of oxygenates to $C_{4+}$ olefins is adjusted to a ratio between 0.05 and 0.5, such as between 0.15 and 0.3. This ratio is calculated according to the formula $$V = \frac{\sum_j k_{oxygenate-j} * n_{oxygenate-j}}{\sum_i k_{olefin-i} * n_{olefin-i} + \sum_j k_{oxygenate-j} * n_{oxygenate-j}}$$

with:
$k_{oxygenate-j}$: carbon number of the oxygenate j
$n_{oxygenate-j}$: molar flow rate of the oxygenate j
$k_{olefin-i}$: carbon number of the olefin i
$n_{olefin-i}$: molar flow rate of the olefin i Since light olefins simultaneously are formed from the oxygenates in an exothermal reaction and the $C_{4+}$ olefins are cracked to light olefins in an endothermal reaction, energy demand and energy supply are in balance. The energy balance of the entire reaction can be controlled by the optimized adjustment of the ratio of olefins:oxygenates and the reactor thus can be operated at an optimum temperature. The propylene yield thereby is maximized with respect to the chosen pressure and temperature reaction conditions. For this purpose, a constant temperature profile or a temperature profile slightly rising towards the reactor end normally is adjusted, for example a temperature gradient of 480 to 500° C.

From the process according to the invention, several synergy effects are obtained. On the one hand, this is the increase in yield of the valuable products propylene and ethylene without increasing the capacity of the actual cracker plant. On the other hand, the downstream hydrogenation for the conversion of the longer-chain olefins is relieved, since the fraction of the longer-chain olefins can be reduced. This effect in particular can be noticed, when an olefin separation as it is described in WO 2006/048184 A1 is connected to a corresponding plant and the low-olefin product streams can be recirculated directly to the cracker. Finally, there can also be an increase in the yield of aromatics, which may be economically advantageous when it is the objective of the plant to chiefly produce higher aromatics.

A coupling of both basic reactions in the olefin conversion process according to the invention leads to an energetic compensation, as described. For this purpose, on the one hand a maximized quantity of foreign olefins can be introduced into an existing MTP® plant, or on the other hand the case existing even more frequently can be assumed, that due to the presence of a cracker plant olefins are available. These olefins can be converted to propylene with a minimized use of methanol or other oxygenates. The combination of a cracker plant or another plant producing olefin by-products with an olefin conversion plant according to the invention thus allows a customized and scalable propylene production.

In addition, the reactor and the process can greatly be simplified as compared to the classical MTP® process. On the one hand, the reactor only has 3 to 4 catalyst beds as compared to 6 in the standard MTP® reactor. The internal fittings required between the beds for the evaporation cooling can be omitted just like a DME reactor with succeeding partial condensation of the reaction water, which is provided upstream of the MTP® reactor.

A partial recirculation of non-converted olefins provides for processing feed streams with different olefin contents or for producing different quantities of valuable products propylene and ethylene. In a first separating means, a mixture rich in $C_{3-}$ olefins from the product mixture from the reactor therefore is separated from a stream rich in $C_{4+}$ gasoline hydrocarbons. The stream rich in gasoline hydrocarbons, which chiefly includes fractions with a chain length of at least four carbon atoms, subsequently is supplied to a second separating means and is separated there into a stream containing a large part of the $C_4$ compounds, a fraction which chiefly includes compounds with at least five C atoms, and a recycling stream, wherein the recycling stream substantially is composed of $C_4$ to $C_6$ compounds. The recycling stream is at least partly recirculated into the reactor, wherein the molar ratio between the recycling stream and the educt stream containing at least one $C_{4+}$ olefin lies between 0.1 and 1.5.

In an advantageous embodiment of the invention the second separating means is operated at a pressure of 4-15 bar, and the recycling stream is withdrawn via a conduit as side draw, such as in gaseous form, and recirculated directly into a conduit opening into the reactor.

The treatment of the recycling stream is of great importance for the propylene/ethylene yields. Because only $C_{4+}$ olefins can be converted to propylene/ethylene to a noticeable extent, the recycling stream should contain a fraction with a maximum olefin content. Depending on the composition of the educt stream C with respect to the olefins $C_4$ to $C_8$, the feed stream B to the second separating means contains different residual fractions of non-converted $C_4$ to $C_6$ olefins. In the second separating means, the same should be concentrated as much as possible in the recycling stream, in that a rather large part of $C_{4-6}$ paraffins is removed from the circuit in the corresponding product streams A and F.

In a simple case, the second separating means according to the invention is designed as distillation column, wherein the recycling stream is removed as side draw at a suitable position between the position of the feed stream and the column head. The column can be operated at a pressure of a few bar above the reactor pressure, so that the side draw stream can be withdrawn as gas stream and be guided to the reactor without further compression. This has the advantage that a re-evaporation (in the case of a liquid recycling stream) or a compression (in the case of a gaseous recycling stream at low pressure) with a compressor can be omitted.

Typically, fluctuating compositions of the educt stream C or even different educt streams are to be expected in a plant. Hence, temporally different $C_{4-6}$ separation tasks are obtained in the feed stream B to the second separating means, which in the standard circuitry with side draw can only be handled unsatisfactorily. Under these more complex conditions, an integrated distillation column according to the invention should be designed as shown in FIG. 6. This provides for separating a $C_4$ cut in the upper part of the column such that in the lower part the top product, i.e. the recycling stream R, contains an optimum quantity of $C_4$. In the lower part of the column, an optimum quantity of $C_{5-6}$ independently can be directed into the top product, i.e. the recycling stream R. The stream guided from the upper into the lower part can be charged as reflux, when the educt stream C chiefly contains $C_4$ hydrocarbons. However, when the fraction of $C_5$ hydrocarbons in the educt stream C is too high, the stream is to be charged as feed into the middle part, so that a depletion of $C_5$ in the recycling stream R can be effected.

Furthermore, a catalyst must be used according to the invention, which is both able to catalyze the conversion of the oxygenates to low-molecular olefins and acts as cracking catalyst for the $C_{4+}$ olefins. According to the invention, a form-selective zeolite material, in particular an alumosilicate of the pentasil type ZSM-5, is suitable above all for this purpose.

It is also favorable to arrange the catalyst in several, at least two, in some embodiments four catalyst beds in the reactor and thus divide the educt stream into a plurality of partial streams such that each partial stream is guided onto one of the catalyst beds. As a result, a temperature control of each individual stage of the reactor can be effected by proportionately charging gaseous oxygenate to the product stream of the preceding stage. By varying the quantity of oxygenate in proportion to the hydrocarbon/olefin fractions, the charging temperature and the reaction conditions, the exit temperature of each stage thus can be adjusted and controlled for a wide spectrum of conditions of use.

Suitable oxygenates in particular include alcohols, above all methanol, but also mixtures such as for example bioethanol with its impurities or the $C_3$ to $C_6$ alcohols obtained as by-products ("fusel oil") in a bioethanol plant. The process according to the invention thus represents a rare combination of the raw material recovery from fossil energy carriers and the raw material recovery from renewable raw materials. Such combination in particular is advantageous in transitional situations from one energy carrier to the other and allows to compensate variations in productivity in one of the two processes.

According to the invention, the pressure at the inlet of the reactor is adjusted to a value between 1.5 and 10 bar, such as to a value between 1.8 and 5 bar. It can thereby be ensured that both reactions proceed with a particularly high selectivity with regard to propylene.

The higher the pressure, the lower the propylene yield and the less oxygenate is required for adjusting the temperature. In an olefin excess situation it thus is recommendable in particular to raise the pressure to 3 to 5 bar with a propylene yield lower than theoretically possible, in order to lower the dimensions of the apparatuses and hence the compression and investment costs.

The temperature at the outlet of the reactor lies between 460 and 560° C., such as between 480 and 510° C. This temperature window provides for simultaneously carrying out MTP® processes and cracking reactions without the formation of undesired by-products.

Suitable starting substances in particular also include oxygenates, which have been obtained as by-product in the production of ethanol by fermentation and/or in a Fischer-Tropsch synthesis. The educt stream containing $C_{4+}$ olefins can contain at least one $C_2$ to $C_{10}$ olefin, which has been produced as primary product in a Fischer-Tropsch synthesis. The advantageous combination of processes with starting substances both from the field of fossil and of renewable raw materials also can be found here. The water often entrained as undesired by-product especially in the field of renewable raw materials can expediently be used in an olefin conversion process according to the invention, as in this way an additional water stream can wholly or partly be omitted.

Furthermore, the invention also comprises a plant for the production of low-molecular olefins, in particular of ethylene and propylene, with the features of claim 9, which is suitable for carrying out the process according to the invention. In at least one reactor filled with catalyst, an educt stream containing at least one oxygenate and an educt stream containing $C_{4+}$ olefins are simultaneously converted to a product mixture comprising low-molecular olefins and gasoline hydrocarbons, wherein at least one supply conduit of the educt stream containing oxygenates and a supply conduit of the educt stream containing $C_{4+}$ olefins open into this reactor and the ratio of these two educt streams defined according to the invention is adjustable to a value between 0.05 and 0.5 by means of a dosing means.

Because the ratio of the oxygenates with respect to the olefins in the feed is relatively small, only small residual contents of oxygenates are present in the product mixture of the reactor. The treatment of the product mixture therefore can considerably be simplified in part as compared to the classical MTP® process.

An according aspect of the invention provides that downstream of the reactor a first separating means is provided for separating the product mixture obtained into a mixture rich in $C_{3-}$ olefins and a mixture rich in $C_{4+}$ gasoline hydrocarbons. This first separating means is followed by a second separating means for separating the mixture rich in $C_{4+}$ gasoline hydrocarbons into a stream substantially containing $C_4$ fractions, a stream rich in $C_{5+}$ gasoline hydrocarbons, and a recycling stream containing above all $C_4$ to $C_6$ olefins. It was found to be favorable when a return conduit leads from this second separating means back to the reactor. In this return conduit a dosing means is provided, with which the molar ratio between the recycling stream poor in aromatics and the educt stream containing $C_{4+}$ olefins is adjustable to a value between 0.1 and 1.5. Thus, highmolecular gasoline hydrocarbons still can be converted into the target products ethylene and propylene by cracking.

It also lies within the scope of the invention to design the second separating means in the form of an integrated column, wherein in the upper part a $C_4$ cut is separated as top product via a conduit, in the lower part the bottom product is charged as reflux or feed via a conduit, and in the lower part a $C_{4-6}$ cut is withdrawn as top product via a conduit and a $C_{5+}$ cut is withdrawn as bottom product via a conduit.

The reactor can be configured as typical reactor for a heterogeneously catalyzed reaction in a gas phase, like for example a tube bundle reactor or also a fixed-bed reactor. It was found to be particularly advantageous to design the reactor as fixed-bed reactor, wherein the catalyst is arranged in a plurality of individual, at least two, such as four, fixed catalyst beds. One conduit each opens into these individual stages of the reactor, via which conduits parts of the educt stream containing oxygenates flow in. These conduits are charged by a dosing device. Each stage, in particular the stages 1 and 2, is designed for a minimum residence time/reserve capacity. The fourth stage is a safety stage, which serves for the reaction of the oxygenates. $C_{6+}$ olefins likewise are reacted, since the same can be recirculated only in part or not at all.

In an embodiment the invention provides for a process for the production of low-molecular olefins, in particular of ethylene and propylene, wherein an educt stream (O) containing at least one oxygenate and an educt stream (C) containing at least one $C_{4+}$ olefin are simultaneously converted in at least one identical reactor on an identical catalyst to obtain a product mixture (P) comprising low-molecular olefins and gasoline hydrocarbons, wherein the ratio (V) of oxygenates in the educt stream (O) to $C_{4+}$ olefins in the educt stream (C) is 0.05 to 0.5, wherein the ratio (V) is calculated according to the formula $$V = \frac{\sum_j k_{oxygenate-j} * n_{oxygenate-j}}{\sum_i k_{olefin-i} * n_{olefin-i} + \sum_j k_{oxygenate-j} * n_{oxygenate-j}}$$

with
$k_{oxygenate-j}$: carbon number of the oxygenate j
$n_{oxygenate-j}$: molar flow rate of the oxygenate j
$k_{olefin-i}$: carbon number of the olefin i
$n_{olefin-i}$: molar flow rate of the olefin i In an embodiment, in a first separating means the product mixture (P) is separated into a mixture (H) rich in $C_{3-}$ olefins and a stream (B) containing $C_{4+}$ olefins, that in a second separating means the stream (B) containing $C_{4+}$ olefins is separated into a stream (F) substantially containing $C_4$ fractions, a stream (A) rich in $C_{5+}$ gasoline hydrocarbons, and a recyling stream (R), (in an embodiment, containing above all $C_4$-$C_6$ olefins), and that the recycling stream (R) is at least partly recirculated to the at least one reactor, wherein the molar ratio between the recycling stream (R) and the educt stream (C) containing $C_{4+}$ olefins lies between 0.1 and 1.5.

In an embodiment, the second separating means is operated at a pressure of 4-15 bar, and the recycling stream (R) is withdrawn as side draw, and recirculated directly into a conduit opening into the reactor.

In an embodiment, the recycling stream is in a gaseous form.

In an embodiment, the educt stream (O) containing oxygenates is divided into several partial streams and each partial stream is passed onto one of at least two-catalyst beds in the reactor.

In an embodiment, the educt stream (O) containing oxygenates is divided into several partial streams and each partial stream is passed onto one of four catalyst beds in the reactor.

In an embodiment, as catalyst a form-selective zeolite material is used.

In an embodiment, an alumosilicate of the pentasil type ZSM-5 is used.

In an embodiment, the educt stream (O) containing oxygenates contains at least one alcohol, such as methanol.

In an embodiment, the pressure at the inlet of the reactor lies between 1.5 and 10 bar, such as between 1.8 and 5 bar.

In an embodiment, the temperature at the outlet of the reactor lies between 460 and 560° C., such as between 480 and 510° C.

In an embodiment, the educt stream (O) containing oxygenates contains at least one oxygenate which has been obtained as by-product in the production of ethanol by fermentation and/or in a Fischer-Tropsch synthesis, and/or that the educt stream (C) containing $C_{4+}$ olefins contains at least one $C_4$ to $C_{10}$ olefin, which has been obtained as primary product in a Fischer-Tropsch synthesis.

In an embodiment, the plant for the production of low-molecular olefins, in particular of ethylene and propylene, in particular for carrying out a process according to any of the preceding claims, comprising at least one catalytic reactor for the simultaneous conversion of an educt stream (O) containing at least one oxygenate and an educt stream (C) containing at least one $C_{4+}$ olefin, into which at least one supply conduit of the educt stream (O) and a supply conduit of the educt stream (C) open, wherein at least one dosing means with which the ratio of oxygenates to $C_{4+}$ olefins is adjustable to a value between 0.05 and 0.5.

In an embodiment, a first separating means for separating the reaction mixture obtained in the reactor into a mixture rich in $C_{3-}$ olefins and a mixture containing $C_{4+}$ olefins, a second separating means for separating the mixture containing $C_{4+}$ olefins into a stream substantially containing $C_4$ fractions, a stream rich in $C_{5+}$ gasoline hydrocarbons, and a recycling stream (in an embodiment, containing above all $C_4$-$C_6$ olefins), a return conduit which leads from the second separating means to the reactor, and a dosing means with which the molar ratio between the recycling stream (R) and the educt stream (C) is adjustable to a value between 0.1 and 1.5.

In an embodiment, the second separating means is designed in the form of an integrated column, wherein in the upper part a $C_4$ cut is separated as top product via a conduit, in the lower part the bottom product is charged as reflux or feed via a conduit, and in the lower part a $C_{4-6}$ cut is withdrawn as top product via a conduit and a $C_{5+}$ cut is withdrawn as bottom product via a conduit.

In an embodiment, a reactor can be designed as fixed-bed reactor with at least two, and in some embodiments four fixed catalyst beds and at least one dosing means for dividing the educt stream (O) containing oxygenates onto conduits which each open before one of the fixed catalyst beds.

Further developments, advantages and possible applications of the invention can also be taken from the following description of exemplary embodiments and the drawings. All features described and/or illustrated form the subject-matter of the invention per se or in any combination, independent of their inclusion in the claims or their back-reference.

DETAILED DESCRIPTION

Figure 1:
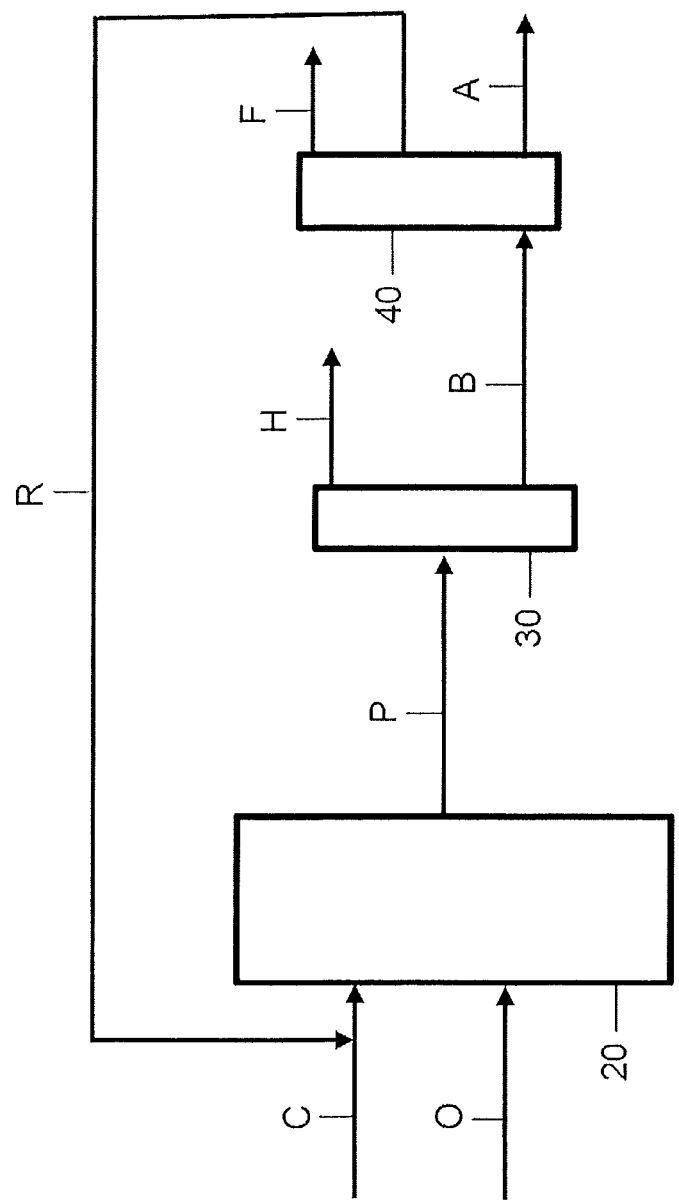
FIG. 1 shows the basic process diagram.

FIG. 1 shows the basic process diagram. An educt stream O containing at least one oxygenate and an educt stream C containing at least one $C_{4+}$ olefin are introduced into a reactor 20 and simultaneously converted there on a solid catalyst, such as an alumosilicate of the pentasil type ZSM-5. The resulting product stream P subsequently is introduced into a first separating device 30. In this separating device 30, the stream P is separated into a mixture H rich in $C_{3-}$ olefins and a mixture B rich in $C_{4+}$ gasoline hydrocarbons. The stream B subsequently is introduced into a second separating device 40 and is separated there into a stream F substantially containing $C_4$ fractions, a stream A rich in $C_{5+}$ gasoline hydrocarbons, and a recycling stream R. The recycling stream R, which can chiefly contains $C_4$ to $C_6$ olefins in gaseous form, subsequently is at least partly recirculated into the reactor 20.

Figure 2:
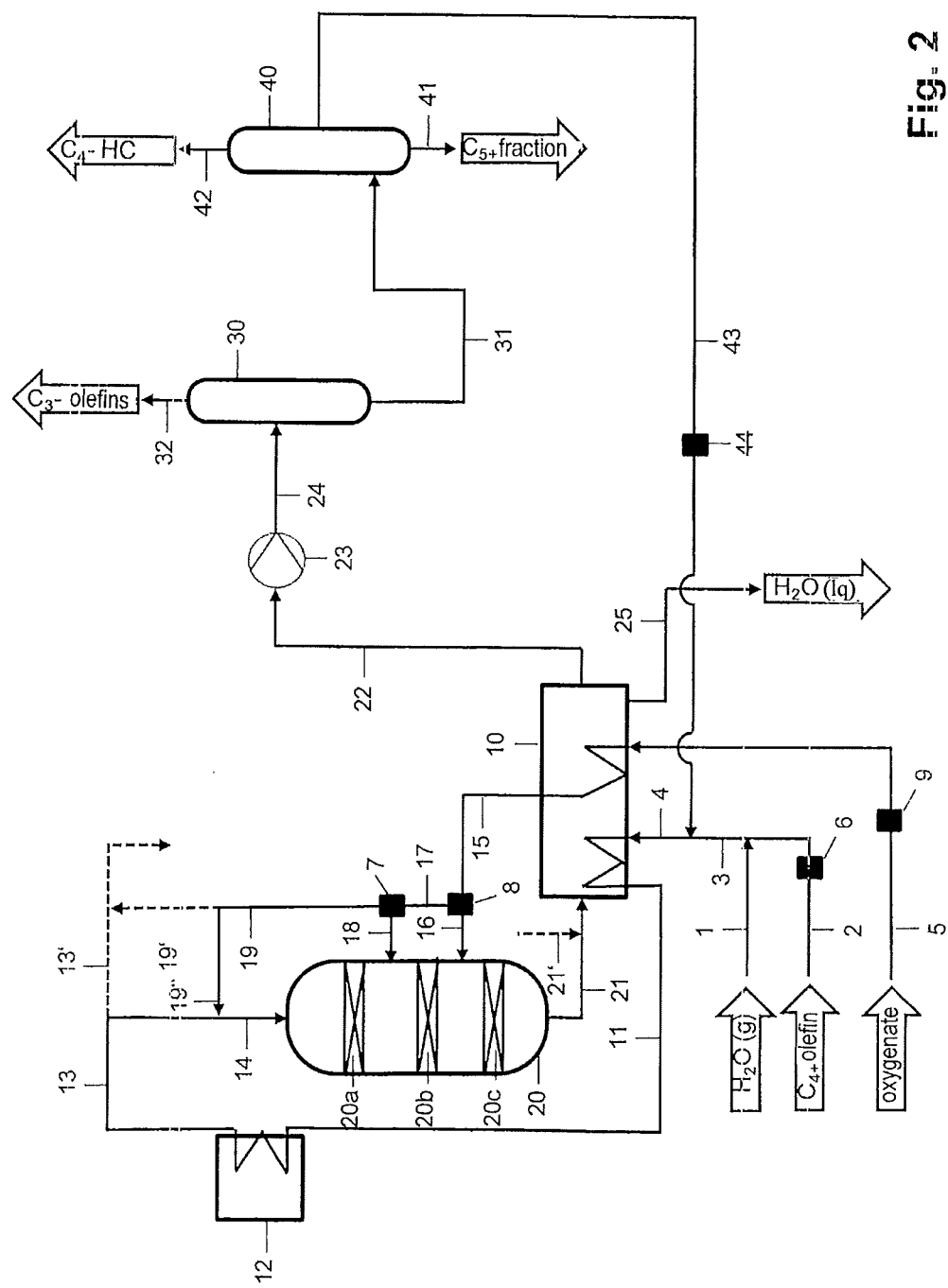
FIG. 2 schematically shows a plant according to the invention with two downstream separating means.

FIG. 2 shows the configuration of a plant according to the invention. For this purpose, a stream containing water, such as water evaporated already, is admixed via conduit 1 to a stream containing at least one $C_{4+}$ olefin in conduit 2. Via conduit 3 and conduit 4, the mixture of these streams is fed into a heat exchanger 10 and preheated there. The quantity of $C_{4+}$ olefin is controlled via the dosing device 6. A likewise present dosing means for the steam is not shown in the Figure. In addition, an oxygenate stream supplied via conduit 5 and dosing means 9 is evaporated and possibly superheated in this heat exchanger 10.

Via conduit 11, the olefin/steam stream is delivered into an undergrate firing 12 and from there via conduits 13 and 14 passed on into the reactor 20. The quantity of the stream is adjusted via dosing devices in the conduits 1 and 2 as well as 43.

Via conduit 15, the pre-evaporated and optimally superheated oxygenate stream enters into a dosing device 8, from where it is fed in directly before the fixed catalyst beds 20b and 20c via conduit 16 and conduit 18. Via conduit 19, it is also possible to at least partly introduce the oxygenate stream into the olefin/steam mixture preheated to the reactor inlet temperature and along with the same guide it into the reactor 20 upstream of the catalyst bed 20a.

The quantity of the oxygenate stream is to be put into the relation to the olefin quantity contained in the olefin stream as defined according to the invention, which is why the oxygenate stream must be dosed in by control devices such as 7 or 8. This dosing or allocation to the individual fixed catalyst beds is effected such that the temperature of a reaction gas stream exiting from a bed is adjusted to the desired value by dosing the oxygenates before the bed. The last catalyst bed 20c is designed with a low load of oxygenates, so that the oxygenate conversion there becomes almost quantitative. Corresponding to the $C_{4+}$ olefin content and the fraction of the supplied oxygenate, a decrease or increase in temperature by few degrees Celsius each is obtained across a bed, whereby across the entire reactor 20 a temperature difference of about −5 to +13° C. is obtained.

In principle, it would also be conceivable to at least partly directly feed the stream containing water into the reactor 20 via conduit 1, which would require a further dosing device for the supplied quantity of water. At least partly admixing the stream of water into the oxygenate stream also is conceivable in principle.

It is likewise conceivable to guide a part of the $C_{4+}$ olefin educt stream from conduit 2 or a part of the olefin-containing recycling stream from conduit 43 to conduit 5 or directly to one or more of the conduits 18, 16, 16' and hence supply it to the reactor 20. This would also require at least one further dosing means.

Via conduits 13' and 19' parts of the educt streams also can be introduced into a parallel reactor, and via conduit 19" parts of the stream from conduit 19 can be fed into conduit 14. Here as well, a dosing means is possible. Parallel reactors on the one hand serve to buffer the aging behavior of the catalyst by regenerating reactors at different times. A parallel reactor either can be operated just like the reactor 20 or also have another configuration, for example include another quantity of fixed catalyst beds. Such parallel connection of reactors provides for a greater flexibility of the plant with regard to the converted mass flows.

Via conduit 21', a product stream obtained in a possibly existing parallel reactor can be admixed to the product stream from reactor 20 in conduit 21. The sum of the product streams enters into the heat exchanger 10 via conduit 21 and hence at the same time is utilized to heat the educt streams.

In the heat recovery device 10—a likewise existing integrated final cooler is not shown in the Figure—a separation of the aqueous phase from the organic phase also is effected already. Via conduit 22, the gas phase is supplied to a compressor 23, from where it is delivered into a first separating device 30 via conduit 24. In the separating device 30, the product mixture compressed to about 25 bar initially is separated into the $C_{3-}$ olefins and a fraction of the longer-chain olefins. While the $C_{3-}$ olefins are discharged via conduit 32, the bottom product with the longer-chain olefins is delivered via conduit 31 into the second separating device 40, which just like the separating device 30 can be is designed as distillation column. In this second separating device 40, the $C_4$ hydrocarbons are separated as top product and the hydrocarbons containing at least five carbon atoms ($C_{5+}$ hydrocarbons) are separated as bottom product. From the separating device 40, a return stream with a rather high residual content of $C_4$ to $C_6$ olefins is recirculated into conduit 3 via conduit 43. The quantity of this stream is determined via the control means 44. In an embodiment, the return stream is recirculated to the reactor in gaseous form. For this purpose, the separating means 40 is operated at a pressure of about 4 bar above the reactor pressure, and via conduit 43 a partial gas stream is withdrawn from the separating means at a suitable position.

Figure 6:
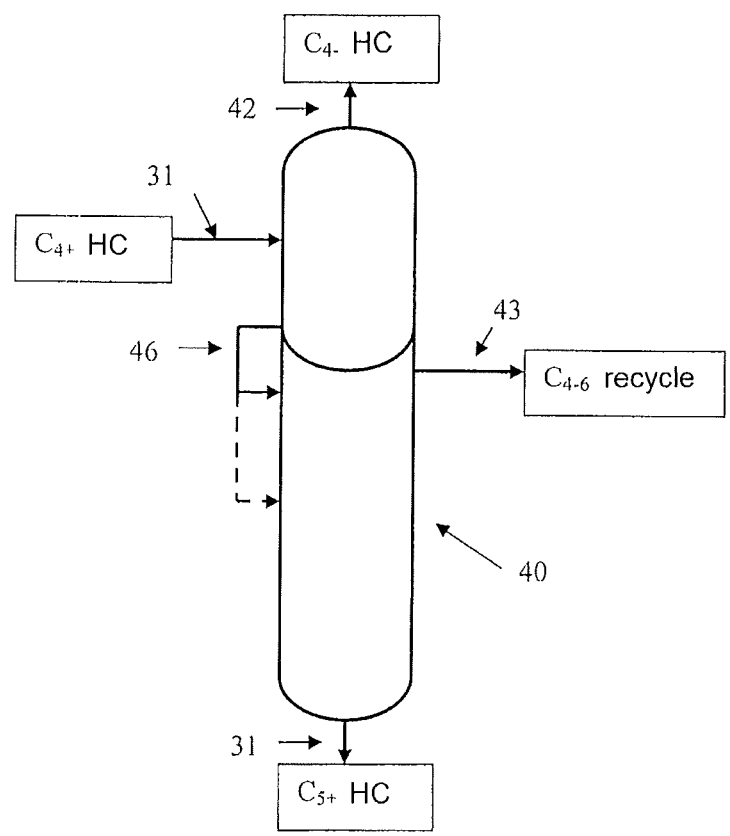
FIG. 6 schematically shows a configuration of the separating unit 40 as integrated distillation column.

When the separating unit 40 is designed as integrated distillation column as shown in FIG. 6, a $C_4$ fraction is withdrawn via conduit 42, wherein the quantity is determined by the reboiler at the upper part of the column. Via conduit 46, the residual quantity of $C_4$ is delivered into the lower part of the column along with $C_5$ hydrocarbons and via conduit 43 is guided to the reactor with an advantageous quantity of $C_{5-6}$ hydrocarbons. Via the control of the reboiler at the lower part of the column it is determined which part of the $C_{5+}$ hydrocarbons is guided to the top of the column or is recovered as bottom product. The fraction $C_{6+}$ rich in aromatics chiefly is discharged from the process as product via conduit 31.***

In the unit for heat recovery 10, steam is condensed and separated from the reaction gases. In a non-illustrated stripper, a fraction containing oxygenates can be recovered from the aqueous condensate and be recirculated into the reactor 20.

The minimum configuration shown in FIG. 2 can be employed above all in cases with a comparatively low use of oxygenates. A residual content of highly volatile reaction products, e.g. dimethyl ether (DME), compromising the propylene product can be separated with the bottom product propane at the latest in the non-illustrated $C_3$ splitter without a particular expenditure of apparatus.

Figure 3:
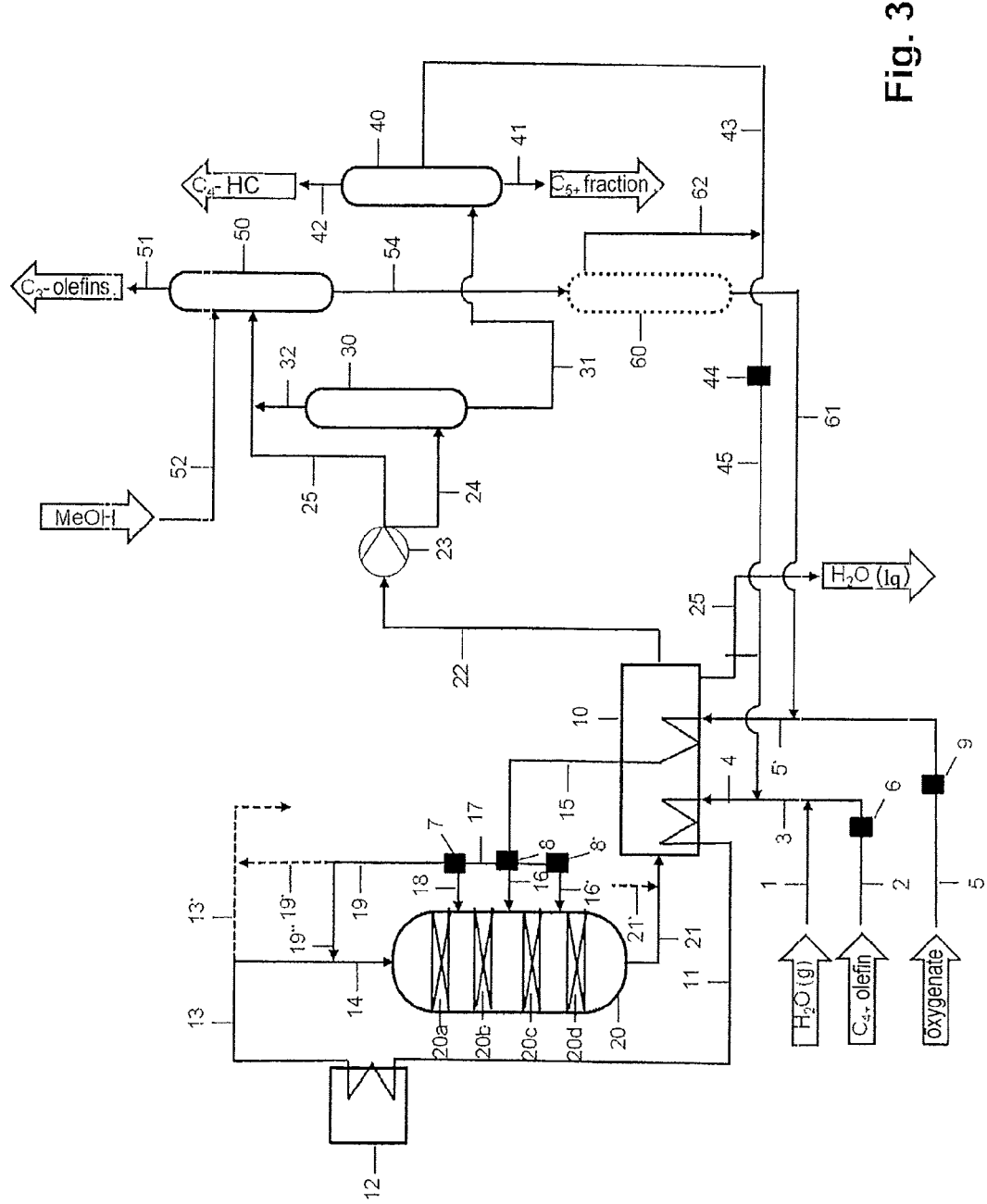
FIG. 3 schematically shows a plant according to the invention with four downstream separating means.

If this is not possible, because particular requirements are to be satisfied by the propane product or because a high propylene yield should be produced with a very high oxygenate feed, a more expensive configuration can be employed, which is shown in FIG. 3.

The construction of the reactor unit is similar to the one described already in FIG. 2. However, the reactor is provided as four-stage reactor, which is why a further partial oxygenate stream is fed into the reactor 20 via conduit 16' and dosing device 8'.

After the compression to about 25 bar in the compressor 23, the product streams initially are supplied via the conduits 24 and 25 to a separating device consisting of the columns 30 and 50. This separating means is described in DE 10 2008 058 931 A1 and by means of a washing agent—here methanol—separates the product mixture into a $C_{3-}$ fraction free from oxygenates (conduit 51), a $C_{4+}$ stream (conduit 31), and the washing agent chiefly loaded with DME/$C_{4-5}$ hydrocarbons (conduit 54). Via conduit 24, the liquid product stream is guided to the separating device 30 and divided into a short-chain fraction ($C_{3-}$ olefins) and a long-chain fraction ($C_{4+}$ olefins). Via conduit 32, the short-chain fraction is admixed to conduit 25 and the combined stream—containing the entire $C_{3-}$ olefin yield—is supplied, to the separating means 50. There, residual quantities of $C_{4+}$ hydrocarbons are separated from the $C_{3-}$ top product and at the same time highly volatile oxygenates, above all DME, are quantitatively removed from the $C_{3-}$ product by means of an oxygenate washing agent, such as methanol. The $C_{3-}$ olefins then are discharged via conduit 51.

In the further course—going beyond DE 10 2008 058 931 A1—the methanol/oxygenate/olefin stream is admixed either directly via conduit 61 to the oxygenate feed in conduit 5 and via conduit 5' fed into the apparatus for heat recovery 10. Or an additional separating device 60 is connected, by which the contained $C_{4-5}$ olefins can be separated and can be withdrawn via conduit 62. Conduit 62 opens into conduit 43, whereby the united olefin stream can be recirculated into conduit 3 via conduit 44. The methanol bottom product of the column 60 is admixed to the oxygenate feed via conduit 61. The separation of $C_{4-5}$ hydrocarbons from methanol has the effect that the hydrocarbons can be supplied to the reactor at a high temperature and accordingly improve the energy balance at very low oxygenate/olefin ratios. On the other hand, a further separating device 60 can be omitted with a relatively high oxygenate feed, because due to the "dilution" of the oxygenate by olefins a stronger cooling effect is achieved before charging the same to the catalyst bed, which is desirable with high oxygenate feeds.

Via conduit 31, the longer-chain hydrocarbons from the separating means 30 are introduced into a separating device 40, in which the $C_4$ hydrocarbons are separated from the $C_{5+}$ hydrocarbons. From the top of the distillation column 40 $C_4$ hydrocarbons are discharged via conduit 42, while the $C_{5+}$ hydrocarbons leave the column via conduit 41 from the bottom of the column 40. Via conduit 43, a recycling stream furthermore can be recirculated from the column 40 via conduit 44 into conduit 3. The position of the conduit 43 in the column 40 is determined such that corresponding to the composition of the feed in conduit 31a maximum $C_4$ to $C_6$ fraction of the recycling stream can be adjusted in conduit 43. In an embodiment, the column is operated at a pressure of >4 bar above the reactor pressure, so that the recycling stream can be recirculated to the reactor in gaseous form without compression.

Figure 4:
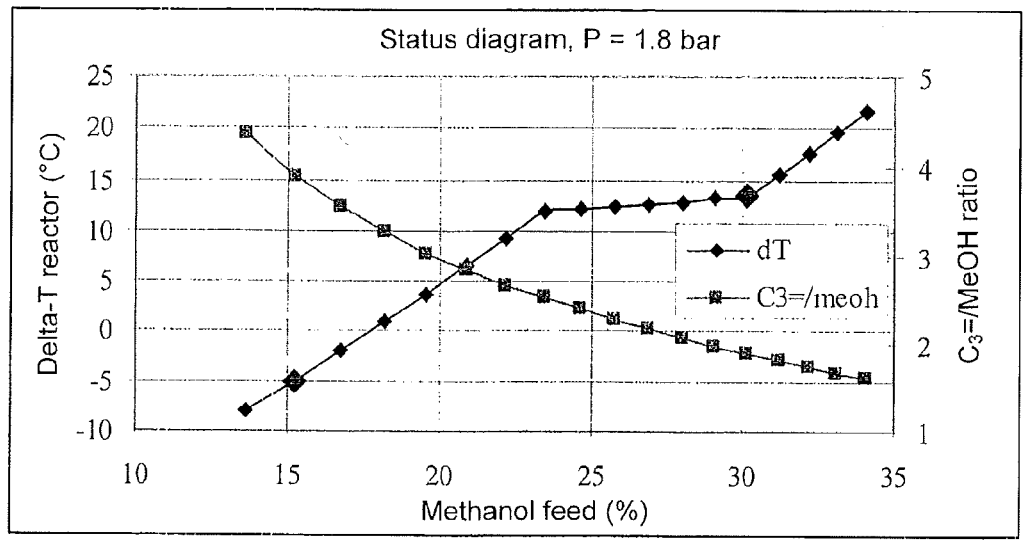
FIG. 4 shows a status diagram for the conversion of a $C_4$ to $C_6$ olefin cut (reactor pressure: 1.8 bar(a))

In FIG. 4, essential ones of the above-mentioned relationships for a typical $C_4$ to $C_6$ olefin cut from a cracker plant are illustrated. At a reactor pressure of 1.8 bar (a), a temperature profile of −5 to +13° C. is obtained across the entire reactor with a methanol feed of 15-30% as defined according to the quantity ratio V of the invention. The temperature holding range is adjusted by different preheating temperatures of the methanol. The propylene:methanol ratio is 3.6-1.5. With a total olefin conversion of 80-75%, the achievable selectivity based on the total quantity of ethylene and propylene is about 59.5-57%.

Like in the MTP® process, a rather low pressure—i.e. about 1.7-1.9 bar (a) at the reactor inlet—promotes the propylene and ethylene yields. However, because $C_{4+}$ olefins in part represent undesired and lower-rated products, the inlet pressure in a reactor according to the invention can be raised to 3-5 bar, without thereby ruining the economy of the process. The high pressure provides for a compact construction of the plant and lower investment costs and costs for resources. Under these boundary conditions, a maximum propylene yield is renounced. The higher the pressure, the lower the propylene yield and the less methanol (oxygenate) is required for adjusting the temperature.

Figure 5:
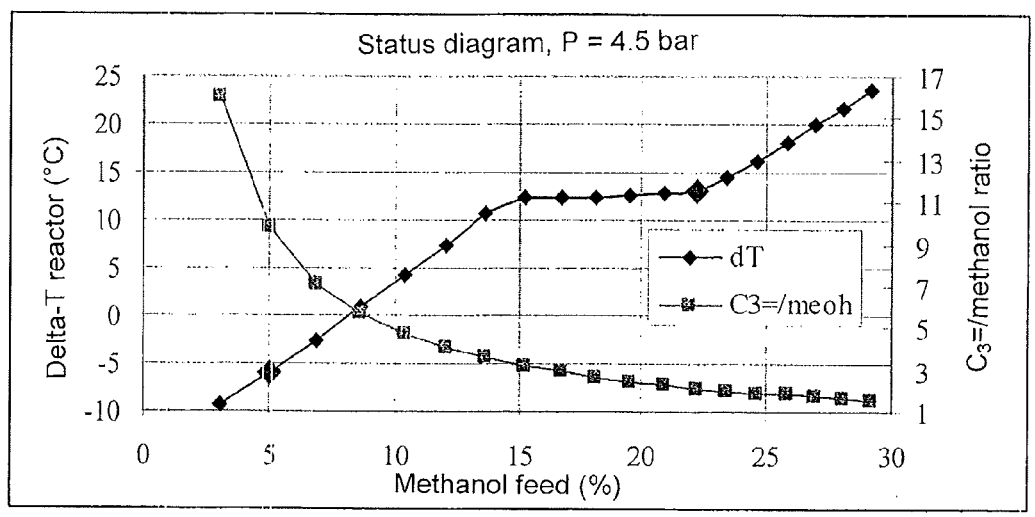
FIG. 5 shows a status diagram for the conversion of a $C_4$ to $C_6$ olefin cut (reactor pressure: 4.5 bar(a))

FIG. 5 shows how at a reactor pressure of 4.5 bar (a) with a methanol feed (=V*100) of 5-23% a temperature profile of −5 to +13° C. is obtained. The propylene:methanol ratio is 10:2. With a total olefin conversion of 85-80%, the achievable selectivity based on the total quantity of ethylene and propylene is about 49-48%.

Example 1

In Example 1 it is assumed that from a $C_{4+}$ olefin cut of 62 t/h with 67 mass-% of olefins, of which 53% are $C_4$ olefins, which is typical for a cracker plant, a rather large quantity of propylene and ethylene should be produced in an economically expedient way. For this purpose, an olefin-methanol conversion plant, as it is shown in FIG. 3, is configured, which should be operated at a reactor pressure of 1.8 bar and a relatively high recirculation rate (1.38) and methanol feed (24%). The reactor target temperature is about 497° C. In the case of only three separating devices 30, 40 and 50 a temperature increase of 7.5° C. is to be expected. The separating unit 40 is designed as integrated column as shown in FIG. 6.

In Table 1a mass balance is listed, and in Table 2 the feed/product quantities and important characteristics of such process are listed.

For the reactor a total height of about 9 m and a diameter of 5.5 m is assumed.

TABLE 1

| Mass balance of a process according to Example 1 | | | | | | | |
|---|---|---|---|---|---|---|---|
| Conduit No. | 2 | 5 | 22 | 51 | 42 | 41 | 43 |
| Mass flow [kg/h] | | | | | | | |
| MEOH | 0.00 | 30000.00 | 397.05 | 0.03 | 0.03 | 0.00 | 32.76 |
| DME | 0.00 | 0.00 | 31.15 | 0.00 | 0.01 | 0.00 | 0.12 |
| H2O | 0.00 | 0.00 | 7557.60 | 0.00 | 0.00 | 0.00 | 309.72 |
| C2H4 | 0.00 | 0.00 | 5377.64 | 5167.57 | 0.00 | 0.00 | 14.79 |

TABLE 1-continued

Mass balance of a process according to Example 1

| Conduit No. | 2 | 5 | 22 | 51 | 42 | 41 | 43 |
|---|---|---|---|---|---|---|---|
| C3H6 | 0.00 | 0.00 | 28059.67 | 27348.31 | 114.82 | 0.00 | 161.19 |
| C4= | 32573.19 | 0.00 | 19543.05 | 0.00 | 4584.01 | 0.92 | 13874.14 |
| C5= | 3886.99 | 0.00 | 10551.97 | 0.00 | 10.38 | 3027.11 | 7389.67 |
| C6-C8= | 5056.42 | 0.00 | 3403.66 | 0.00 | 0.00 | 2320.84 | 1079.64 |
| CH4 | 0.00 | 0.00 | 204.66 | 198.50 | 0.00 | 0.00 | 0.43 |
| C2 | 0.00 | 0.00 | 41.09 | 40.69 | 0.00 | 0.00 | 0.03 |
| C3 | 84.76 | 0.00 | 1559.61 | 1483.84 | 26.14 | 0.00 | 35.34 |
| C4 | 12755.22 | 0.00 | 67131.53 | 0.00 | 15199.85 | 4.17 | 47307.18 |
| C5 | 2745.57 | 0.00 | 15839.87 | 0.00 | 62.77 | 3964.12 | 11600.37 |
| C6-C8 | 4728.04 | 0.00 | 9380.06 | 0.00 | 0.00 | 6391.67 | 2984.28 |
| Aromatics | 163.61 | 0.00 | 5425.31 | 0.00 | 0.00 | 4981.30 | 449.28 |
| H2 | 0.00 | 0.00 | 23.94 | 23.92 | 0.00 | 0.00 | 0.00 |
| CO | 0.00 | 0.00 | 214.74 | 214.57 | 0.00 | 0.00 | 0.01 |
| Inert gases | 0.00 | 0.00 | 3.25 | 3.20 | 0.00 | 0.00 | 0.00 |
| Oxygenates | 0.00 | 0.00 | 217.29 | 0.00 | 0.00 | 42.33 | 160.77 |
| Total flux [kmol/h] | 1012.50 | 936.27 | 3435.75 | 901.08 | 347.55 | 245.44 | 1405.48 |
| Total flux [kmol/h] | 61993.80 | 30000.00 | 174963.00 | 34480.62 | 19998.00 | 20732.46 | 85399.70 |
| Total flux [m³/h] | 108.90 | 38.51 | 88989.03 | 777.43 | 43.65 | 29.82 | 2759.70 |
| Temperature [° C.] | 53.38 | 30.00 | 50.00 | 45.08 | 98.95 | 38.09 | 105.29 |
| Pressure [bar] | 18.00 | 1.00 | 1.02 | 23.00 | 17.00 | 13.18 | 12.80 |
| Steam fraction | 0.00 | 0.00 | 1.00 | 1.00 | 0.00 | 0.00 | 1.00 |
| Liquid fraction | 1.00 | 1.00 | 0.00 | 0.00 | 1.00 | 1.00 | 0.00 |
| Enthalpy [J/kg] | −1.20E+06 | −7.45E+06 | −1.65E+06 | 4.88E+05 | −1.91E+06 | −1.37E+06 | −1.60E+06 |
| Density [kg/m³] | 569.27 | 779.08 | 1.97 | 44.35 | 458.18 | 695.28 | 30.95 |
| Mean molecular mass | 61.23 | 32.04 | 50.92 | 38.27 | 57.54 | 84.47 | 60.76 |

TABLE 2

Feed and product quantities for Examples 1, 2 and 3

| | Unit | Example 1 | Example 2 | Example 3 |
|---|---|---|---|---|
| Feed | t/h | 62.0 | 62.0 | 40.0 |
| Type of feed | | $C_4$-$C_6$ | $C_4$-$C_6$ | $C_4$ |
| Olefin content | % | 67.0 | 67.0 | 50.0 |
| Type of oxygenate | | methanol | methanol | $C_1$-$C_5$ alcohols |
| Oxygenate quantity | t/h | 30.0 | 9.0 | 9.0 |
| Propylene | t/h | 27.4 | 17.7 | 10.1 |
| Ethylene | t/h | 5.2 | 3.6 | 2.1 |
| C4 | t/h | 20.0 | 19.0 | 16.0 |
| C4+ or C5+ | t/h | 20.7 | 21.9 | 15.0 |
| Oxygenate (methanol) fraction | % | 24.0 | 8.7 | 17.8 |
| Propylene/oxygenate ratio | | 2.5 | 5.4 | 2.9 |
| Propylene selectivity | % | 59.4 | 46.8 | 51.9 |
| Olefin conversion | % | 76.1 | 81.2 | 70.8 |

Example 2

In Example 2, a reconstruction of an existing cracker plant into a plant according to the invention (revamp situation) is assumed. From the same $C_{4+}$ olefin cut as in Example 1 additional quantities of propylene and ethylene should be produced with a minimum of investment costs. At the same time, the mass flow and olefin content of the $C_{4+}$ streams should be reduced distinctly, in order to save the capacity of the downstream processing plants. For this purpose, an olefin/methanol conversion plant, as shown in FIG. 2, is configured, which should be operated at a reactor pressure of 4.5 bar and a mean recirculation rate (1.0) and only 9% methanol feed. The reactor target temperature is about 497° C. Here as well, the separating unit 40 is designed as integrated column according to FIG. 6.

In Table 2, the feed/product quantities and important characteristics are listed. For the reactor a total height of about 7 m and a diameter of 3.4 m is assumed. As compared to Example 1, the dimensions of the downstream plants up to the compressor are reduced correspondingly.

Example 3

In this example, too, a revamp situation is assumed in a cracker plant. From a $C_{4+}$ olefin cut (40 t/h, 50% olefin content), additional quantities of propylene and ethylene should be produced with a minimum of investment costs. In this case, 3 t/h of alcohol mixture with $C_2$ to $C_5$ alcohols, which are obtained as by-product in a bioethanol plant, are available beside methanol. For this purpose, an olefin/methanol conversion plant, as it is shown in FIG. 2, is configured, which should be operated at a reactor pressure of 4.5 bar and a mean recirculation rate (1.0). The oxygenate fraction is 29%. The reactor target temperature is about 484° C.; the temperature profile across the reactor is −4.5° C. The slight decrease in temperature in this case above all is due to the fact that the alcohol mixture also contains ethanol, which in a highly endothermal reaction chiefly is converted to ethylene. In Table 2, the feed/product quantities and important characteristics are listed.

For the reactor a total height of about 7 m and a diameter of 2.8 m is assumed.

Example 4

In Table 3, characteristic data for various olefin conversion plants according to the invention are listed and compared with the Propylur process. In the example, the same $C_{4+}$ cut as in Examples 1 and 2 is used as feed. With respect to the yields of propylene and ethylene and the consumption of resources, distinct, in part drastic advantages of the process of the invention as compared to the Propylur process are to be noted. The same also would apply for the OCP process. In these examples, the separating unit 40 is designed as simple column with gaseous side draw.

TABLE 3

Comparison of the process according to the invention with the Propylur process

|  | Recycling stream [t/h] | Steam [t/h] | Alcohol [t/h] | Yield[1] (ethylene + propylene) [t/h] | Yield[1] (ethylene + propylene) [mole-%] | Consumptions of resources | | |
|---|---|---|---|---|---|---|---|---|
|  |  |  |  |  |  | Steam[2] | Furnace[3] | Compressor |
| Propylur | 31.0 | 141.0 |  | 19.8 | 47.2 | 146.0 | 17.0 | 3.8 |
| Olefin conversion 500° C. 3.5 bar | 88.0 | 30.0 | 23.0 | 27.6 | 53.5 | 50.5 | 20.5 | 3.5 |
| Olefin conversion 500° C. 4.5 bar | 90.0 | 30.0 | 13.0 | 23.2 | 49.2 | 51.0 | 17.0 | 2.1 |
| Olefin conversion with bioethanol[4] 485° C., 4.5 bar[4] | 88.0 | 30.0 | 20.0 | 27.4 | 52.8 | 51.0 | 20.0 | 2.6 |

[1]calculated for alcohols and olefins
[2]including process steam generation
[3]drive power
[4]alcohol feed: 50% crude bioethanol (incl. $C_3$ to $C_6$ alcohols), 50% methanol; ethanol chiefly provides ethylene. Yields are estimated values.

Example 5

In a Fischer-Tropsch plant (F-T plant) olefins and alcohols are obtained as by-products. The same are hydrogenated or used for undergrate firing purposes. In an olefin conversion plant according to the invention, which is integrated with the F-T plant, the olefin- and alcohol-containing streams can be used for propylene production. The yields are shown in Table 4.

TABLE 4

Comparison of the process according to the invention in combination with an F-T plant to a stand-alone F-T plant on the basis of 80000 barrels/day

|  | Olefin-containing hydrocarbons [t/h] | F-T alcohols [t/h][(2)] | Methanol [t/h] | Yield[1] ($C_3$) [t/h] |
|---|---|---|---|---|
| Standard F-T | 35.3 | — | — | 2.5 |
| F-T + olefin conversion | 35.3 | 7.3 | 10.0 | 10.0 |

[1]$C_3$ yield converted into $C_3$ (propylene) (99.9%)
[2]alcohol content 35%

List of Reference Numerals
1-5 conduits
6-9 dosing devices
10 heat recovery device
11 conduit
12 undergrate firing
13-19 conduits
20 reactor
20a-d fixed catalyst beds
21-22 conduits
23 compressor
24-25 conduits
30 separating means
31-32 conduit
40 separating means
41-43 conduits
44 dosing device
45 conduit
46 conduit
50 separating means
51, 52, 54 conduits
60 separating means
61 conduit
O oxygenate-containing educt stream
C stream containing $C_{4+}$ olefins
P product stream
H $C_{3-}$ olefin stream
B stream containing $C_{4+}$ olefins
F stream containing $C_4$ olefins
A stream containing $C_{5+}$ olefins
R recycling stream containing $C_{4-6}$ olefins

The invention claimed is:

1. A process for the production of ethylene and propylene comprising, simultaneously converting an educt stream (O) containing at least one oxygenate and an educt stream (C) containing at least one $C_{4+}$olefin in at least one identical reactor over an identical catalyst to produce a product mixture (P) comprising low-molecular olefins and gasoline hydrocarbons,
   separating the product mixture (P) in a first separation unit to recover a mixture (H) rich in ethylene and propylene, and a stream (B) comprising $C_{4+}$olefins;
   separating the stream (B) comprising $C_{4+}$olefins in a second separation unit to recover a stream (F) rich in $C_4$ paraffins, a stream (A) rich in $C_{5+}$gasoline hydrocarbons, and a recycle stream (R) comprising $C_4$, $C_5$, and $C_6$ olefins; and
   recycling a portion of the recycle stream (R) comprising $C_4$, $C_5$, and $C_6$ olefins to the identical reactor, the molar ratio between the recycling stream (R) and the educt stream (C) containing $C_{4+}$olefins comprises between 0.1 and 1.5;
   wherein the ratio (V) of oxygenates in the educt stream (O) to $C_{4+}$olefins in the educt stream (C) is 0.05 to 0.5, wherein the ratio (V) is calculated according to the formula $$V = \frac{\sum_{j} k_{oxygenate-j} * n_{oxygenate-j}}{\sum_{i} k_{olefin-i} * n_{olefin-i} + \sum_{j} k_{oxygenate-j} * n_{oxygenate-j}}$$

with $k_{oxygenate-j}$: carbon number of the oxygenate j
$n_{oxygenate-j}$: molar flow rate of the oxygenate j
$k_{olefin-i}$: carbon number of the olefin i
$n_{olefin-i}$: molar flow rate of the olefin i.

2. The process according to claim 1, wherein the second separation unit is operated at a pressure of 4-15 bar, and the recycling stream (R) is withdrawn as side draw, and recirculated directly into a conduit opening into the reactor.

3. The process according to claim 1, wherein the educt stream (O) containing oxygenates is divided into several partial streams and each of the partial streams is passed onto a different catalyst bed of at least two catalyst beds in the reactor.

4. The process according to claim 1, wherein as catalyst a form-selective zeolite material is used.

5. The process according to claim 1, wherein the educt stream (O) containing oxygenates contains at least one alcohol.

6. The process according to claim 1, wherein the pressure at the inlet of the reactor lies between 1.5 and 10 bar.

7. The process according to claim 1, wherein the temperature at the outlet of the reactor lies between 460 and 560° C.

8. The process according to claim 1, wherein the educt stream (O) containing oxygenates contains at least one oxygenate which has been obtained as by-product in the production of ethanol by fermentation and/or in a Fischer-Tropsch synthesis, and/or that the educt stream (C) containing $C_{4+}$olefins contains at least one $C_4$ to $C_{10}$ olefin, which has been obtained as primary product in a Fischer-Tropsch synthesis.

9. The process according to claim 2, wherein the recycling stream is in gaseous form.

10. The process according to claim 3, wherein each partial stream is passed onto four catalyst beds in the reactor.

11. The process according to claim 4, wherein an alumosilicate of the pentasil type ZSM-5, is used.

12. The process according to claim 5, wherein the at least one alcohol comprises methanol.

13. The process according to claim 6, wherein the pressure at the inlet of the reactor lies between 1.8 and 5 bar.

14. The process according to claim 7, wherein the temperature at the outlet of the reactor lies between 480 and 510° C.

* * * * *